United States Patent
Shimomura et al.

[11] Patent Number: 5,854,396
[45] Date of Patent: Dec. 29, 1998

[54] PROTEIN, DNA CODING FOR SAME AND METHOD OF PRODUCING THE PROTEIN

[75] Inventors: Takeshi Shimomura; Toshiya Kawaguchi; Naomi Kitamura, all of Kanagawa, Japan

[73] Assignee: Mitsubishi Chemical Corporation, Tokyo, Japan

[21] Appl. No.: 974,196

[22] Filed: Nov. 19, 1997

Related U.S. Application Data

[62] Division of Ser. No. 685,660, Jul. 24, 1996, Pat. No. 5,731,412.

[30] Foreign Application Priority Data

Jul. 24, 1995 [JP] Japan ..................... 7-187134

[51] Int. Cl.$^6$ ............. C07K 1/00; C12N 15/15; C12N 15/79
[52] U.S. Cl. ............. 530/350; 435/691; 435/252.3; 435/320.1; 536/23.7; 935/11; 935/32; 935/70
[58] Field of Search ............. 530/350; 536/23.2; 435/69.1, 252.3, 320.1

[56] References Cited

U.S. PATENT DOCUMENTS 5,466,593  11/1995  Shimomura et al. ............. 435/219
5,731,412  3/1998  Shimomura et al. ............. 530/350

OTHER PUBLICATIONS

Neldini et al., *EMBO J.*, 11:4825–4833 (1992).
Ponte et al, *Nature*, 331:525–527 (1988).
Shimomura et al, *Eur. J. Biochem*, 229:257–261 (1995).
Hillier et al, "The WashU–Merck EST Project", Accession No. R74593 (Seq. Ref. No. HS593137) (1995).
Hillier et al, "The WashU–Merck EST Project", Unpublished Data Entry No. H94519 (1995).
Hillier et al, "The WashU–Merck EST Project", Unpublished Data Entry No. W94849 (1995).
Hillier et al, "The WashU–Merck EST Project", Unpublished Data Entry No. N57450 (1995).
Hillier et al, "The WashU–Merck EST Project", Accession No. R35464 (Seq. Ref. No. HS46499) (1995).
Hillier et al, "The WashU–Merck EST Project", Accession No. H39798 (Seq. Ref. No. HS798277) (1996).
Miyazawa et al, *Journal of Biological Chemistry*, 268(14):10024–10028 (1993).
Miyazawa et al, *Journal of Biological Chemistry*, 271(7):3615–3618 (1996).

*Primary Examiner*—Robert A. Wax
*Assistant Examiner*—William Moore
*Attorney, Agent, or Firm*—Sughrue, Mion, Zinn, Macpeak & Seas, PLLC

[57] ABSTRACT

A novel protein having inhibitory activity on the protease activity of hepatocyte growth factor (HGF) activator was purified and isolated, and its molecular weight (ca. 30,000 daltons) and partial amino acid sequence were determined. A gene coding for the protein was cloned, and the gene DNA was incorporated into a vector, for transforming host cells. Cultivation of the transformant gave the desired protein. The protein can be used as an in vivo or in vitro control factor for HGF or HGF activator. It is also useful as an antigen to be used in producing an antibody to be used as means for kinetic studies of the protein, or as a standard in assay systems therefor.

3 Claims, 2 Drawing Sheets

PROTEIN, DNA CODING FOR SAME AND METHOD OF PRODUCING THE PROTEIN

This is a Divisional of patent application Ser. No. 08/685,660, filed Jul. 24, 1996, now U.S. Pat. No. 5,731,412.

FIELD OF THE INVENTION

The present invention relates to a novel protein and a DNA coding for the same. More particularly, it relates to a novel protein having inhibitory activity on the protease activity of hepatocyte growth factor activating factor (HGF activator) (hereinafter this protein is sometimes referred to also as "HAI-II"), a gene coding for the protein, an expression vector containing the gene, a transformant as transformed with the expression vector, and a method of producing HAI-II using the transformant.

BACKGROUND OF THE INVENTION

It is already reported that thrombin activates the precursor of HGF activator (JP-A-5-103670, JP-A-6-141859, JP-A-6-153946 and JP-A-6-153966 (the term "JP-A" as used herein means an "unexamined published Japanese patent application")); factor having activity to convert the single chain form of hepatocyte growth factor (HGF) to its double chain form) in the manner of positive activity control. However, any human tissues-derived protease inhibitor capable of inhibiting, as a negative control factor, the physiological activity of HGF activator has not been known. Therefore, how HGF activator is controlled in human tissues remains unknown. Such a negative control factor might also influence indirectly on the activity of hepatocyte growth factor (HGF) on which HGF activator acts. Thus, for the analysis of the mechanism of action of HGF in vivo, as well, it has been demanded that such a human tissues-derived protease inhibitor be isolated and identified.

By using such a protease inhibitor and an antibody to the protease inhibitor, it would become possible to know the in vivo physiological activity of HGF activator, analyze the mechanism of action thereof or analyze the mechanism of control of HGF activation, from a standpoint different from those of the prior art.

Furthermore, for investigating the detailed in vivo function of HAI-II or the effect of HAI-II in hepatic disorder, for instance, HAI-II is required in large quantities. At present, however, there is only one method available for preparing HAI-II, which method comprises using, as a starting material, the culture supernatant obtained with a human cancer cell line such as MKN45 or A549 cells and purifying therefrom HAI-II occurring therein in trace amounts. This method is not always the best one from the labor, time and cost viewpoint. It encounters great difficulties in stably isolating the minor amount of HAI-II alone. Therefore, it has been desired that an expression system be constructed so that HAI-II can be obtained stably and in large quantities.

SUMMARY OF THE INVENTION

The present inventors have conducted screening of various cultured cell lines using, as an indicator, the inhibitory activity on the protease activity of hepatocyte growth factor activator and have found that a substance having the activity occurs in the culture supernatant of certain human cancer cell lines (MKN45 cells, A549 cells and like epithelial tumor cell lines). To reveal the nature of its inhibitory activity, they further attempted to purify the substance from the MKN45 cell culture supernatant using various column chromatography techniques. As a result, they have found a novel protein with a molecular weight of about 30,000 daltons as determined by SDS (sodium dedecyl sulfate)-polyacrylamide gel electrophoresis(PAGE) and, they also have obtained an amino-terminal amino acid sequence of this protein by analyzing the protein on a protein sequencer. Further, they determined partial amino acid sequences by decomposing the protein using proteolytic enzymes, isolating the resultant peptides and subjecting each peptide to the same amino acid sequence analysis as mentioned above. Furthermore, they estimated DNA base sequences based on the partial amino acid sequences and conducted screening of a cDNA library using oligonucleotide probes prepared based on the sequences. As a result, they have succeeded in cloning a gene coding for the protein and have now completed the present invention.

Furthermore, as a result of various investigations to produce the protein stably and in large quantities using the recombinant DNA technique and, the present inventors have constructed a novel expression vector coding for the protein and have enabled expression of the protein. Thus, by constructing a plasmid for protein expression by inserting a DNA fragment coding for part or the whole of the amino acid sequence of the protein into a plasmid vector such as the expression vector pME18S for use in animal cells or an expression vector for use in yeasts, *Escherichia coli* and the like, at a site downstream from the promoter thereof and using the thus-obtained recombinant plasmid to transform host cells, they have now completed the present invention in another aspect.

The present invention thus relates to a protein having the following physico-chemical properties:

(1) a molecular weight of about 30,000 daltons as determined by SDS-polyacrylamide gel electrophoresis;

(2) inhibitory activity on the protease activity of hepatocyte growth factor activator; and (3) one of the amino acid sequences depicted in the sequence listing under SEQ ID NO:1 through 3 or an amino acid sequence substantially equivalent thereto; proteins respectively having the amino acid sequences depicted in the sequence listing under SEQ ID NO:1 through 3 or amino acid sequences substantially equivalent thereto and having inhibitory activity on the protease activity of hepatocyte growth factor activator; a protein having the amino acid sequence depicted in the sequence listing under SEQ ID NO:4 or an amino acid sequence substantially equivalent thereto; and a protein having, as its amino acid sequence, that segment of the amino acid sequence depicted in the sequence listing under SEQ ID NO:4 which starts with the 28th amino acid (alanine) residue and ends with the 252nd amino acid (leucine) residue, or an amino acid sequence substantially equivalent thereto; DNAs and genes coding for the proteins defined above; expression vectors respectively containing the DNA or genes; transformants obtained by transformation of host cells with the expression vectors; as well as a method of producing proteins having inhibitory activity on the protease activity of hepatocyte growth factor activator which comprises cultivating the transformants.

The base sequence shown in the sequence listing under SEQ ID NO:4 contains only one strand, with the other complementary base sequence being omitted. Starting with this gene and using the recombinant DNA technology, it is possible to cause expression of, for example, the protein having the amino acid sequence shown in the sequence listing under SEQ ID NO:4. On that occasion, the protein translated from mRNA coding for the protein contains a signal sequence. After extracellular excretion, however, the signal sequence has been cleaved off and the protein obtained has an amino acid sequence comprising the 28th amino acid (alanine) residue and the subsequent amino acid residues of the amino acid sequence shown in the sequence listing under SEQ ID NO:4. Signal sequences of other proteins may also be used as the signal sequence. For signal sequence-free mature protein expression in host cells, a gene having that portion of the base sequence shown in the sequence listing under SEQ ID NO:4 which comprises the 82nd nucleotide (guanine) residue and the subsequent nucleotide residues may be used as the gene coding for the relevant protein and joined to the ATG codon of a vector. The present invention further includes, within the scope thereof, modifications of the proteins or DNAs mentioned above as derived therefrom by deletion, substitution and/or addition of one or more amino acid or nucleotide residues within limits not harmful to the inhibitory activity on the protease activity of HGF activator, namely those proteins or DNAs that respectively have "substantially equivalent amino acid sequences" or "substantially equivalent base sequences".

DETAILED DESCRIPTION OF THE INVENTION

Figure 1:
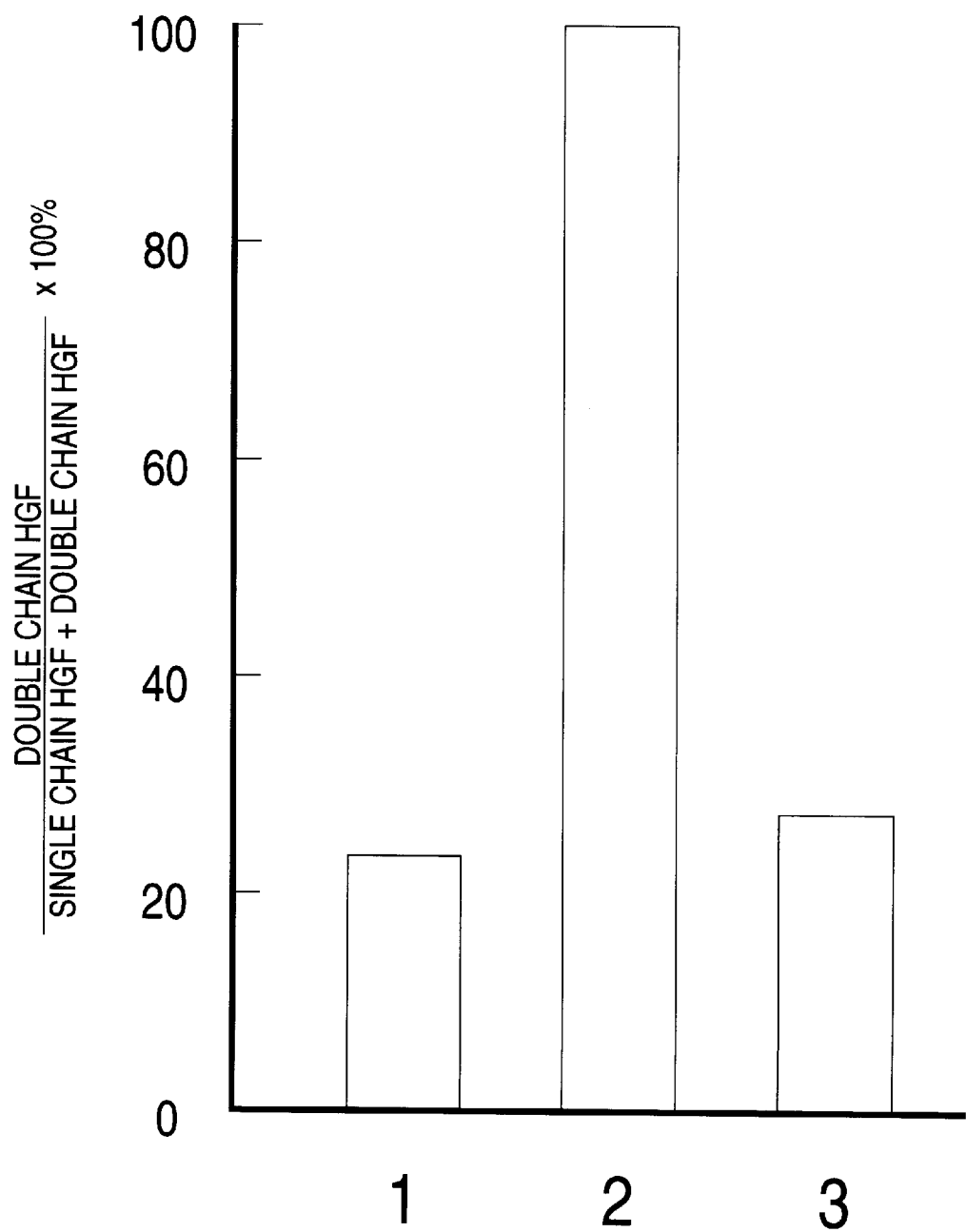
FIG. 1 shows the results of assaying of the protein of the present application for its inhibitory activity on the protease activity of HGF activator.

In the following, the present invention is described in further detail. The novel protein of the present invention which has protease inhibitor activity can be obtained by proceeding via such purification steps as mentioned below. For example, a human cancer cell line (MKN45 cells or A549 cells deposited with the Japanese Cancer Research Resources Bank under the deposite numbers JCRB0254 and JCRB0076, respectively, or like epitherlial tumor cell line) is cultivated in a serum-free medium for several days, the culture supernatant is recovered and, after removal of cells therefrom and concentration, submitted to a heparin-Sepharose column (available e.g. from Pharmacia). The non-adsorbed fraction is submitted to a ConA-Sepharose column (available e.g. from Pharmacia) and separated into an adsorbed fraction and an non-adsorbed fraction. The non-adsorbed fraction is subjected to hydrophobic chromatography using Phenyl-5PW (available e.g. from Tosoh Corp.). The thus-obtained fraction containing the desired protein is chromatographed on a DEAE ion exchange column (available e.g. from Polymer Laboratory), then submitted to a hydroxyapatite column (available e.g. from Mitsui Toatsu Chemicals or Seikagaku Corp.), and further to gel filtration column chromatography (using e.g. Asahi Chemical Industry's GS520) to give the protein in question. The purification steps may further include reversed phase column chromatography and/or other appropriate means, as necessary.

Upon SDS-polyacrylamide gel electrophoresis, the thus-purified protein of the present invention migrates as a smear band or several fragments presumably resulting from differences in sugar chain, amino acid residue modification and/or C-terminal side mutation and having a molecular weight of about 30,000 daltons. When reacted with HGF activator, the protein shows inhibitory activity on the protease activity of HGF activator. This protein of the present invention contains the amino acid sequence shown in Table 1 below.

A DNA fragment of the gene coding for the novel protein of the present invention can be obtained in the following manner. By analyzing the novel protein purified in the above manner using a gaseous phase protein sequencer (available e.g. from Applied Biosystems), its amino-terminal amino acid sequence can be determined. Further, the protein is decomposed using lysyl endopeptidase (e.g. Achromobacter protease I), the resulting peptide fragments are separated by reversed phase high-performance liquid chromatography (using e.g. a YMC's column) and each fragment is subjected to amino acid sequence analysis in the same manner as mentioned above, whereby the amino acid sequence of an intermediate portion of the protein can be revealed.

A DNA base sequence is deduced from the amino acid sequence thus determined and, correspondingly, appropriate oligonucleotides are synthesized and used as probes. Human-derived liver, spleen and placenta cDNA libraries (available e.g. from Clonetec), among others, can be used as the cDNA library for screening out the gene coding for the desired protein. In addition, a cDNA library may be constructed in the conventional manner from a cell line or tissue material in which the protein is expressed.

*Escherichia coli* is transfected with λ phage containing such cDNA incorporated therein (the method of Maniatis et al.: "Molecular Cloning") and then cultivated. The plaques formed are subjected to selection by plaque hybridization using oligonucleotide probes prepared based on the base sequence deduced from the amino acid sequence of a portion of the protein in question, whereby a certain number of different A phage clones having the amino acid sequence of the desired protein and containing, in addition, those segment base sequences of the protein that correspond to other regions than the probes can be obtained with ease.

Then, the phage from each positive plaque obtained in the above screening is then allowed to replicate by the method of Maniatis et al., and DNA is purified therefrom by the glycerol gradient method and, after appropriate restriction enzyme cleavage, submitted to cDNA subcloning into a plasmid vector such as pUC18 or pUC19 or a single chain phage vector such as M13 mp18 or M13 mp19. Thereafter, the base sequence of the desired cDNA fragment can be determined by the method of Sanger et al. The base sequences of the clones obtained are analyzed and synthesized and, as a result, a gene totally corresponding to the whole amino acid sequence of the desired protein as shown in the sequence listing under SEQ ID NO:4 can be derived from a group of cDNAs coding for respective portions of the protein. It is also possible to obtain a gene containing the whole of the cDNA in question, a gene containing the cDNA with deletion of a partial base sequence thereof, a gene containing the cDNA with insertion of some other base sequence, a gene containing the cDNA with substitution of some other base sequence for a partial base sequence of the cDNA, or the like gene from a variety of cDNA libraries by the PCR method using portions of the cDNA in question as probes. Such site-specific mutation, inclusive of base sequence deletion, addition or substitution, can be readily realized by the methods described in the literature (e.g. Methods in Enzymol., 217, 218 (1993); ibid., 217, 270 (1993)).

The group of cDNAs obtained in the above manner are joined together so that the order of the base sequences is fit to the amino acid sequence of the protein, to give a DNA fragment covering the whole region of the protein. The DNA fragment is inserted into a plasmid, such as pCDL-SRα296, at a site downstream from the promoter thereof and matched in phase with the translation initiation codon ATG, to thereby construct a protein expression vector. Then, the protein can be expressed in a host, for example animal cells, transformed with the plasmid. Thereafter, the protein expressed can be recovered by purification by a conventional method.

Thus, each of the thus-obtained cDNAs is inserted into a plasmid, such as pME18S, at a site downstream from the promoter thereof to thereby construct a plasmid for protein expression. The protein or a protein derived therefrom by partial amino acid sequence deletion, insertion or substitution can be expressed in a host, such as animal cells, transformed with the expression plasmid. More concretely, CHO cells, COS cells, mouse L cells, mouse C127 cells, mouse FM3A cells and the like can be used as the animal cells for protein expression. When these animal cells are used as the host, the use, as a signal sequence, of that portion of the DNA base sequence shown in the sequence listing under SEQ ID NO:4, namely the gene for the protein, which starts with the 1st nucleotide and ends with the 35th nucleotide, or the use of an existing signal sequence is expected to be conducive to extracellular secretory production of the protein or production thereof on the cell membrane.

The expression plasmid for use in animal cell hosts is constructed in the following manner. As the promoter, use can be made of any of the existing promoters, for example the SRα promoter, SV40 promoter or metallothionein gene promoter. A DNA containing the whole gene for the protein, inclusive of the above-mentioned signal-like sequence, a DNA containing the gene with a partial base sequence deletion, a DNA containing the gene with insertion of a base sequence or a DNA containing the gene with substitution of some other sequence for a partial base sequence thereof is inserted into a site downstream from the promoter in the direction of transcription. In constructing the expression plasmid for the protein, two or three pieces of the DNA fragment of the gene coding for the protein may be joined together and used for insertion downstream from the promoter. It is also possible to join such a promoter as the SV40 promoter to the 5' upstream side of the DNA fragment of the gene coding for the protein to give a unit insert and insert, into a vector, two or three such units joined together in the same direction of transcription. A polyadenylation site is added to the downstream side of the gene coding for the protein. For example, the polyadenylation site derived from the SV40 DNA, β-globin gene or metallothionein gene can be joined to the downstream side of the gene coding for the protein. When a DNA fragment comprising a promoter and the gene coding for the protein as joined together is duplicated or triplicated, each unit may contain a polyadenylation site on the 3' side of the gene coding for the protein. In transforming animal cells, for example CHO cells, with such expression vector, a drug resistance gene can be used for the purpose of expression cell selection. As the drug resistance gene, there may be mentioned the DHFR gene which provides resistance to methotrexate (J. Mol. Biol., 159, 601 (1982)), The Neo gene which provides resistance to the antibiotic G-418 (J. Mol. Appl. Genet., 1, 327 (1982)), the *Escherichia coli*-derived Ecogpt gene which provides resistance to mycophenolic acid (Proc. Natl. Acad. Sci. U.S.A., 78, 2072 (1981)) and the hph gene which provides resistance to the antibiotic hygromycin (Mol. Cell. Biol., 5, 410 (1985)), among others. Each resistance gene contains a promoter, such as the above-mentioned SV40-derived promoter, inserted on the 5' upstream side and a polyadenylation site as mentioned above on the 3' downstream side of each resistance gene. In inserting such resistance gene into the expression vector for the protein, the gene may be inserted at a site downstream from the polyadenylation site of the gene coding for the protein, in either direction, the same or opposite. These expression vectors make it unnecessary to perform double transformation with another plasmid containing a selective marker gene for the purpose of transformant isolation. When the expression vector for the protein does not contain such a selective marker gene insert, a vector having a marker suited for transformant selection, for example pSV2neo (J. Mol. Appl. Genet., 1, 327 (1982)), PMBG (Nature, 294, 228 (1981)), pSV2gpt (Proc. Natl. Acad. Sci. U.S.A., 78, 2072 (1981)) or pAd.D26.1 (J. Mol. Biol., 159, 601 (1982)), may be used, in combination with the expression vector for the gene coding for the protein, for transformation to thereby make it easy to perform transformant selection based on phenotypic expression of the drug resistance gene.

The expression vector can be introduced into animal cells by the calcium phosphate method (Virology, 52, 456 (1973)) or the electroporation method (J. Membr. Biol., 10, 279 (1972)), for instance. The transformed animal cells can be cultivated in the conventional manner in the manner of suspension culture or adhesion culture. They are cultivated in a medium such as MEM or RPMI 1640 in the presence of 5 to 10% of serum or in the presence of an appropriate amount of insulin, transferrin or the like, or under serum-free conditions. Further, it is also possible to produce the protein using microorganisms such as yeasts or *Escherichia coli*, for example strains of *Saccharomyces cerevisiae* or the strain *Escherichia coli* YA-21. Since the cells express the protein in the culture supernatant or on the cell surface, it is possible to recover and purify the protein using the culture supernatant or cells of this transformant. More specifically, the protein can be isolated and purified by subjecting the culture supernatant or cell extract containing the protein produced to an appropriate chromatography procedure, for example chromatographic treatment using heparin-Sepharose, ConA-Sepharose, hydroxyapatite and the like in combination.

The protease inhibitor activity-endowed protein of the present invention has inhibitory activity on the protease activity of HGF activator and, therefore, is useful as a in vitro or in vivo regulatory factor for HGF activator or, indirectly, as a HGF activity regulating factor. The protein as well as an antibody to the protein or a gene coding for the protein is further useful as a tool or means for function analysis of the factors.

Furthermore, by introducing an expression vector carrying a gene coding for the protein into animal cells, it becomes possible to produce part or the whole of the protein or a protein equivalent thereto, which is biologically active, in a stable manner and in large quantities. This has so far been difficult to attain.

The present invention is now illustrated in greater detail with reference to the following Examples. However, it is not intended that the present invention be limited to these Examples.

EXAMPLE 1

(Purification of the protein using an MKN45 cell culture supernatant)

MKN45 cells (Naito et al., Gan to Kagaku-ryoho (Cancer and Chemotherapy), 5, 89 (1978)) (obtained from Men-eki Seibutsu Kenkyusho) were seeded into eRDF medium containing 5% FBS (fetal bovine serum) as placed in a roller bottle 850 and allowed to multiplicate until a confluent state was attained. Then, the FBS-containing culture supernatants was removed and the cells were washed with two portions of serum-free eRDF medium. After removing the washing medium, 500 ml of serum-free eRDF medium was added and incubation was carried out at 37° C. for 3 to 6 days. After incubation, the culture supernatants was recovered, 500 ml of fresh serum-free eRDF medium was added, and incubation was again conducted. This procedure was repeated several times. The culture supernatants thus recovered were combined and concentrated about 20-fold using a YM30 ultrafiltration membrane (Amicon).

This concentrate was submitted to a heparin-Sepharose column (equilibrated with PBS) and the non-adsorbed fraction was recovered. This fraction was submitted to a ConA-Sepharose column (equilibrated with PBS) and separated into the non-adsorbed fraction and an adsorbed fraction eluted with a PBS solution containing 200 mM α-methyl-D-mannoside. The ConA non-adsorbed fraction was concentrated using YM30, followed by buffer substitution to 10 mM phosphate buffer (pH 6.8) containing 1M ammonium sulfate. The new solution was subjected to HPLC using Phenyl-5 PW (Tosoh Corp.; equilibrated with 10 mM phosphate buffer (pH 6.8) containing 1M ammonium sulfate), followed by linear concentration gradient elution with 1M ammonium sulfate to 0M ammonium sulfate. A fraction containing the desired protease inhibitor activity was thus recovered.

The fraction was dialyzed against 20 mM Tris-hydrochloride buffer (pH 8) containing 0.05% CHAPS and then subjected to HPLC using DEAE (equilibrated with 20 mM Tris-hydrochloride buffer (pH 8) containing 0.05% CHAPS), followed by linear concentration gradient elution with 0M to 500 mM NaCl, whereby a fraction showing the desired protease inhibitor activity was recovered. The fraction was dialyzed against 5 mM phosphate buffer (pH 6.8) containing 0.05% CHAPS and then subjected to HPLC using a HCA A-4007 column (product of Mitsui Toatsu Chemicals) (equilibrated with 5 mM phosphate buffer (pH 6.8) containing 0.05% CHAPS), and the non-adsorbed fraction was recovered. The fraction was submitted to GS-520 (equilibrated with PBS containing 0.05% CHAPS) and an active fraction (fraction of about 40 to 20 kDa) was recovered. For eliminating minor bands, the fraction was applied to a YMC pack C4 column (obtained from YMC), linear concentration gradient elution was carried out over 40 minutes using acetonitrile-isopropyl alcohol (3/7) containing 0.1% TFA and varying the concentration thereof from 10% to 50%, and the active fraction was neutralized with 1M Tris-hydrochloride buffer (pH 8) and then dried under reduced pressure. After drying, the solid obtained was dissolved in PBS containing 0.05% CHAPS to give a purified protein solution.

EXAMPLE 2
(Amino-terminal amino acid sequence and partial amino acid sequence determination of the protein)

The protein having protease inhibitor activity as purified as in Example 1 and eluted by reversed phase HPLC was dried under reduced pressure without neutralization. This was dissolved in 60 µl of 50% TFA (trifluoroacetic acid), added to a polybrene-treated glass filter and subjected to Edman degradation on an Applied Biosystems model 470A sequencer, and the amino acid sequence of an N-terminal region was determined. Phenylhydantoin (PTH)-amino acids were identified using a Mitsubishi Chemical's MCI gel ODS IHU column (0.46×15 cm) and conducting single solvent elution with acetate buffer (10 mM acetate buffer (pH 4.7), 0.01% SDS, 38% acetonitrile) at a flow rate of 1.2 ml/minute and a temperature of 43° C. PTH-amino acids were detected based on the absorbance at 269 nm.

As a result, the N-terminal amino acid sequence shown below in Table 1 was identified.

Then, the same protein having protease inhibitor activity as purified as in Example 1 and eluted by reversed phase HPLC was dissolved in 100 µl of 50 mM Tris-hydrochloride buffer (pH 9.0) containing 4M urea, lysyl endopeptidase (Achromobacter protease I) was added to the solution, and the reaction was carried out at 37° C. for 8 hours. The resulting peptide mixture was separated by reversed phase HPLC using a YMC pack C8 column (YMC) to give respective peptide fragments. Two peptides were subjected to amino acid analysis using a gaseous phase sequencer (Applied Biosystems model 1470A). The sequences shown in Table 1 were found.

TABLE 1
Amino acid sequences of peptides
 N-terminal: Ala-Asp-Arg-Glu-Arg-Ser-Ile-His-Asp-Phe-Xaa-Leu-Val-Ser-Lys (SEQ ID NO:1 in the sequence listing)
Partial amino acid sequences
 1: Lys-Val-Val-Gly-Arg-Xaa-Arg-Ala-Ser-Met-Pro-Arg-Trp-Trp-Tyr-Asn-Val-Thr-Asp-Gly-Ser-Xaa-Gln-Leu-Phe-Val-Tyr-Gly-Gly (SEQ ID NO:2 in the sequence listing)
 2: Ala-Thr-Val-Thr-Glu-Asn-Ala-Thr-Gly-Asp-Leu-Ala-Thr-Ser-Arg-Asn-Ala-Ala-Asp-Ser-Ser Val-Pro-Ser-Ala-Pro (SEQ ID NO: 3 in the sequence listing)
(Xaa: amino acid residue not yet identified)

EXAMPLE 3
(Purification of the protein using an A549 cell culture supernatant and amino acid sequence analysis)

A culture supernatant was prepared by cultivating A549 cells (obtained from the Japanese Cancer Research Resources Bank) in the same manner as in Example 1. Using the culture supernatant and proceeding in the same manner as in Example 1, a protein having the inhibitory activity on the protease activity of HGF activator was obtained. Upon SDS-PAGE, this protein showed the same molecular weight as that derived from MKN45 cells. When subjected to the same N-terminal amino acid sequence determination as in Example 1, this protein gave the same sequence as that of the MKN45 cell-derived protein. This suggested the possibility of the protein being identical with the MKN45-derived protein.

EXAMPLE 4
(Method of assaying the activity of the protein inhibiting the protease activity of HGF activator as well as the activity)

One to ten µl of the sample to be assayed was added to 30 to 40 µl of PBS-0.05% CHAPS solution containing 2 to 5 ng of serum-derived HGF activator. After 30 minutes of incubation at 37° C., 5 to 10 µg of single chain HGF was added and incubation was further continued for 2 hours. This incubation mixture was subjected to SDS-polyacrylamide gel electrophoresis under reducing conditions. After electrophoresis, Coomassie Brilliant Blue R250 (CBB) staining was performed and the proportions of single chain HGF and double chain HGF were compared for activity detection.

The purified protein (10 ng) and 5 ng of serum-derived HGF activator were incubated in 30 to 40 µl of PBS-0.05%

CHAPS solution at 37° C. for 30 minutes, then 10 μg of single chain HGF was added, and incubation was further continued for 2 hours. The incubation mixture was subjected to SDS-polyacrylamide gel electrophoresis under reducing conditions followed by staining with CBB. The results are shown in FIG. 1. In the figure, the numeral 1 indicates the case where neither of HGF activator and the protein was added, 2 indicates the case where HGF activator was added but the protein was not added, and 3 indicates the case where HGF activator and the protein were added. Addition of the protein resulted in suppression of the activity of HGF activator converting single chain HGF to double chain HGF.

EXAMPLE 5
(SDS-polyacrylamide gel electrophoresis)

For determining the apparent molecular weight of the protein having protease inhibitor activity as purified from the MKN45 cell culture supernatant or A549 cell culture supernatant in Example 1 or Example 2, the protein was subjected to SDS-polyacrylamide gel electrophoresis. The protein finally purified was subjected to SDS-polyacrylamide gel electrophoresis using 12.5% polyacrylamide slab gels, which was conducted under nonreducing conditions. The molecular weight markers used were Molecular weight markers "Daiichi" III for Laemmli method (Daiichi Pure Chemicals). After electrophoresis, color development was performed using a silver stain reagent (Kanto Chemical). Upon relative comparison in migration distance between the protein and the molecular weight markers, the protein obtained from the MKN45 cell culture supernatant or A549 cell culture supernatant showed several fragments or a smear band, presumably due to differences in sugar chain, amino acid residue modification or terminal region, at positions around an apparent molecular weight of about 30,000 daltons as determined by SDS-polyacrylamide gel electrophoresis.

EXAMPLE 6
(Cloning of a gene coding for the protein and base sequence determination)

The following two oligonucleotide primers were designed based on a presumption that Xaa will be Cys from the standpoint of the sequences Lys-Val-Val-Gly-Arg-Xaa-Arg and Xaa-Gln-Leu-Phe-Val-Tyr-Gly-Gly selected from the partial amino acid sequence (SEQ ID NO:2 in the sequence listing) of the protein obtained in Example 2.

Primer 1: 5'-AAGGTNGTNGGNMGNTGYMG-3' (SEQ ID NO: 5 in the sequence listing); and
Primer 2: 5'-CNCCGTANACGAANARYTGRC-3' (SEQ ID NO: 6 in the sequence listing).

(In the above sequences, N indicates T or G, M indicates A or C, Y indicates T or C, and R indicates A or G.)

Then, total RNA was prepared from MKN45 cells by the method described in Anal. Biochem., 162, 156 (1987) and applied to an oligo(dT)-cellulose column, whereby poly(A) +RNA was obtained.

Using the thus obtained poly (A)+RNA as the template, RT-PCR (reverse transcription-polymerse chain reaction; cf. K. Hayashi (ed.): "PCR Ho no Saishin Gijutu (State-of-art Techniques of PCR)", page 44 and page 52, published Feb. 5, 1995 by Yohdosha) was carried out. The reaction mixture obtained by this RT-PCR was analyzed by polyacrylamide gel electrophoresis, whereupon a DNA fragment of about 85 bp was detected. Therefore, this DNA fragment was extracted from the polyacrylamide gel, followed by phenol-chloroform extraction and ethanol precipitation, whereby the DNA fragment was recovered. The base sequence of the DNA fragment was determined by the dideoxy method. Further, this DNA fragment was labeled with $^{32}p$ by the method described in "Molecular Cloning" (Cold Spring Harbor Laboratory, 1982) and used as a screening probe.

Using the MKN45 cell line-derived poly(A)+RNA together with a cDNA synthesis kit (Pharmacia), cDNA was synthesized, and a phage library was constructed, as a library for screening, with λ ZAPII (Strategene) as the vector. *Escherichia coli* XL Blue (Strategene) was infected with the above phage library to give about 100,000 plaques.

After overnight culture in NZY medium, the bacterial cells were transferred to a Gene Screening Plus membrane (du pont). The membrane was placed on a filter paper impregnated with 0.1M sodium hydroxide-0.5M Tris hydrochloride buffer (pH 7.5) and allowed to stand for 2 minutes and then placed on a filter paper impregnated with 1.5M sodium chloride-0.5M Tris hydrochloride buffer (pH 7.5) and allowed to stand for 5 minutes. After two more repetitions of this series of treatments, the membrane was washed with 2×SSC (two-fold concentrated SSC) and air-dried on a dry filter paper. This membrane was irradiated with UV light at a dose of 120 mJ/cm$^2$ for fixation of the DNAs transferred to the membrane. The thus-treated membrane was immersed in 50 ml of a solution comprising 50 mM Tris hydrochloride buffer (pH 7.5), 1M sodium chloride and 1% SDS and maintained in that state at 65° C. for 2 hours. Then, the membrane was immersed in 40 ml of a solution comprising 5 ng/ml of the above-mentioned $^{32}$p-labeled probe, 100 μg/ml of salmon sperm, 50 mM Tris hydrochloride buffer (pH 7.5), 1M sodium chloride and 1% SDS and maintained in that state at 65° C. for 16 hours. Thereafter, this membrane was washed with 2×SSC at room temperature over 5 minutes and then with two portions of 0.1×SSC at room temperature over 30 minutes, and subjected to autoradiography, which gave 22 positive clones supposedly containing cDNA for the protein. Then, each positive clone was submitted to plasmid construction by the excision method (Toyobo Life Science Catalog, pages 114–115) according to Toyobo Life Science Catalog (pages 114–115) and Strategene's manual.

The thus-obtained plasmid DNAs were then cleaved with the restriction enzyme EcoRI and subjected to agarose gel electrophoresis, and a clone with the longest cDNA for the protein inserted therein was selected. Then, by analyzing the base sequence of the plasmid (pHAI-II) harbored by this clone, the whole base sequence of the gene coding for the protein was determined (SEQ ID NO:4 in the sequence listing).

EXAMPLE 7
(Preparation of an expression plasmid for the protein)

Figure 2:
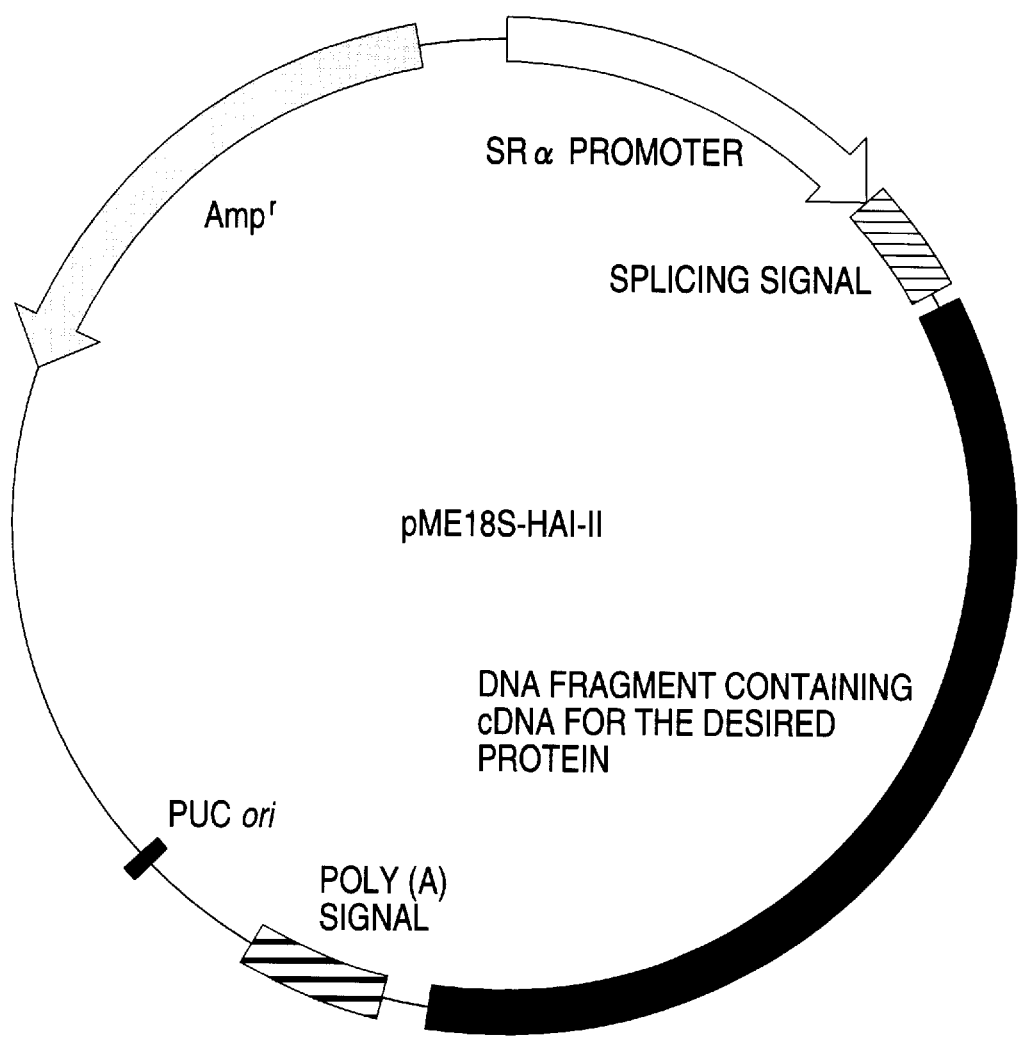
FIG. 2 shows the structure of the plasmid pME18S-HAI-II.

A 10-μg portion of the plasmid (pHAI-II) containing the cDNA for the protein as obtained in Example 6 was subjected to cleavage with the restriction enzyme EcoRI, followed by agarose gel electrophoresis. Thus, an about 1.4 kb EcoRI-EcoRI DNA fragment containing the cDNA for the protein was separated and extracted. The thus-obtained DNA fragment was rendered blunt-ended by the conventional method using T4 DNA polymerase and, then, the DNA fragment was purified by phenol-chloroform extraction and ethanol precipitation and dissolved in 10 μl of water. Separately, 0.05 μg of the expression vector pME18S (Medical Immunology, 20, 27 (1990)) was cleaved in advance with the restriction enzyme XhoI and the DNA fragment obtained was rendered blunt-ended by the conventional method using T4 DNA polymerase and then purified by phenol-chloroform extraction and ethanol precipitation. This was dissolved in 400 μl of a 1 mM $MgCl_2$ solution in 50 mM Tris-HCl (pH 8), 1 unit of bacterial alkaline phosphatase (Toyobo, BAP-101) was added, and dephosphorylation treatment was conducted at 65° C. for 30 minutes. Then, the DNA fragment was purified from this reaction mixture by phenol-chloroform extraction and ethanol precipitation and dissolved in 10 μl of water. Ligation reaction was carried out in 20 μl of a reaction mixture (66 mM Tris-HCl, pH 7.6, 6.6 mM $MgCl_2$, 10 mM dithiothreitol, 66 μM ATP) containing 0.01 μg of the pME18S vector-derived DNA fragment prepared as mentioned above and 0.1 μg of the above-mentioned blunt-ended EcoRI fragment of cDNA for the protein in the presence of T4 DNA ligase (Toyobo LGA-101) at 14° C. for 12 hours. A 10-μl portion of this T4 DNA ligase reaction mixture was used to transform *Escherichia coli* HB101 (Takara Shuzo) according to the manual attached thereto. The microorganism was cultured on a medium containing 50 μg/ml of ampicillin and scores of ampicillin-resistant strains were obtained. These transformants were analyzed by the method of Maniatis et al. ("Molecular Cloning", Cold Spring Harbor Laboratory, pages 86–96 (1982)) and, as a result, a plasmid, pME18S-HAI-II, containing the gene coding for the protein as inserted at the XhoI restriction enzyme cleavage site occurring between the promoter and polyadenylation site of the expression vector pME18S could be obtained. Its structure is shown in FIG. 2.

EXAMPLE 8

(Obtaining of a cell line expressing the protein)

The plasmid pME18S-HAI-II constructed in Example 7 and containing the cDNA for the protein as inserted at the XhoI restriction enzyme cleavage site of the expression vector pME18S was recovered and purified from the recombinant *Escherichia coli* by the method of Maniatis et al. ("Molecular Cloning", Cold Spring Harbor Laboratory, pages 86–96 (1982)) and thus a large amount of the expression plasmid DNA for the protein was obtained. COS cells were transformed by transfection thereof with the expression plasmid DNA. Thus, COS cells were first cultured in eRDF medium containing 10% FBS (fetal bovine serum) in tissue culture dishes 9 cm in diameter until a semiconfluent condition. Then, the medium was removed from the dishes, and a DNA solution prepared as mentioned below was added dropwise thereto as mentioned below. First, for each dish 9 cm in diameter, a solution was prepared in an Eppendorf centrifuge tube by adding thereto 300 μl of 2×HEBS solution (2×HEBS solution: 1.6% sodium chloride, 0.074% potassium chloride, 0.05% disodium hydrogen phosphate dodecahydrate, 0.2% dextrose, 1% HEPES (pH 7.05)) and 10 μg of the plasmid DNA and making the volume 570 μl with sterilized water. Then, while adding 30 μl of 2.5M calcium chloride solution to the DNA solution, the tube contents were stirred vigorously using a vortex mixer for several seconds. The resulting mixture was allowed to stand at room temperature for 30 minutes, with occasional stirring at intervals of about 10 minutes using a vortex mixer. The thus-prepared DNA solution was laid on the cells mentioned above and the whole was allowed to stand at room temperature for 30 minutes. Then, 9 ml of eRDF medium (Kyokuto Pharmaceutical) supplemented with 10% FBS was added to each dish and incubation was performed at 37° C. for 4 to 5 hours in the presence of 5% $CO_2$. Then, the medium was removed from each dish and the cells were washed with 5 ml of 1×TBS++ solution (1×TBS++ solution: 25 mM Tris-hydrochloride (pH 7.5), 140 mM sodium chloride, 5 mM potassium chloride, 0.6 mM disodium hydrogen phosphate, 0.08 mM calcium chloride, 0.08 mM magnesium chloride). After removing the 1×TBS++ solution, the cells were covered with 5 ml/dish of 1×HEBS solution containing 10% DMSO (dimethyl sulfoxide) and allowed to stand at room temperature for 1 to 2 minutes. The supernatant was then removed. The cells were again washed with 5 ml of 1×TBS++ solution, 10 ml of eRDF medium supplemented with 10% FBS was added to each dish and incubation was performed at 37° C. in the presence of 5% $CO_2$. After the lapse of 48 hours, the medium was recovered. The supernatant recovered was 20-fold concentrated and assayed for inhibitory activity against HGF activator in the same manner as in Example 4. The inhibitory activity was confirmed.

While the invention has been described in detail and with reference to specific embodiments thereof, it will be apparent to one skilled in the art that various changes and modifications can be made therein without departing from the spirit and scope thereof.

What is claimed is:

1. A substantially pure protein having the following physico-chemical properties:

(1) a molecular weight of about 30,000 daltons, as determined by SDS-polyacrylamide gel electrophoresis;

(2) inhibits hepatocyte growth factor activator protease activity; and (3) the amino acid sequences set forth in SEQ ID NO:1, SEQ ID NO:2 and SEQ ID NO:3.

2. A substantially pure protein having the amino acid sequence shown in SEQ ID NO:7.

3. A substantially pure protein having the amino acid sequence from amino acid 28 (alanine) to amino acid 252 (leucine) shown in SEQ ID NO:7.

* * * * *

SEQUENCE LISTING ( 1 ) GENERAL INFORMATION:

( i i i ) NUMBER OF SEQUENCES: 7

( 2 ) INFORMATION FOR SEQ ID NO:1:

( i ) SEQUENCE CHARACTERISTICS:
        ( A ) LENGTH: 15 amino acids
        ( B ) TYPE: amino acid
        ( D ) TOPOLOGY: linear (ii) MOLECULE TYPE: peptide (v) FRAGMENT TYPE: N-terminal fragment (vi) ORIGINAL SOURCE:
    (A) ORGANISM: Homo sapiens
    (B) STRAIN: MKN45

(x) SEQUENCE DESCRIPTION: SEQ ID NO: 1:

```
Ala  Asp  Arg  Glu  Arg  Ser  Ile  His  Asp  Phe  Xaa  Leu  Val  Ser  Lys
 1                    5                        10                        15
```

(2) INFORMATION FOR SEQ ID NO:2:

(i) SEQUENCE CHARACTERISTICS:
        (A) LENGTH: 29 amino acids
        (B) TYPE: amino acid
        (D) TOPOLOGY: linear (ii) MOLECULE TYPE: peptide (v) FRAGMENT TYPE: internal fragment (vi) ORIGINAL SOURCE:
        (A) ORGANISM: Homo sapiens
        (B) STRAIN: MKN45

(x) SEQUENCE DESCRIPTION: SEQ ID NO: 2:

```
Lys  Val  Val  Gly  Arg  Xaa  Arg  Ala  Ser  Met  Pro  Arg  Trp  Trp  Tyr  Asn
 1                    5                        10                        15
Val  Thr  Asp  Gly  Ser  Xaa  Gln  Leu  Phe  Val  Tyr  Gly  Gly
                     20                        25
```

(2) INFORMATION FOR SEQ ID NO:3:

(i) SEQUENCE CHARACTERISTICS:
        (A) LENGTH: 26 amino acids
        (B) TYPE: amino acid
        (D) TOPOLOGY: linear (ii) MOLECULE TYPE: peptide (v) FRAGMENT TYPE: internal fragment (vi) ORIGINAL SOURCE:
        (A) ORGANISM: Homo sapiens
        (B) STRAIN: MKN45

(x) SEQUENCE DESCRIPTION: SEQ ID NO: 3:

```
Ala  Thr  Val  Thr  Glu  Asn  Ala  Thr  Gly  Asp  Leu  Ala  Thr  Ser  Arg  Asn
 1                    5                        10                        15
Ala  Ala  Asp  Ser  Ser  Val  Pro  Ser  Ala  Pro
                     20                        25
```

(2) INFORMATION FOR SEQ ID NO:4:

(i) SEQUENCE CHARACTERISTICS:
        (A) LENGTH: 759 base pairs
        (B) TYPE: nucleic acid
        (C) STRANDEDNESS: double
        (D) TOPOLOGY: linear (ii) MOLECULE TYPE: cDNA to mRNA (iv) ANTI-SENSE: no (v) ORIGINAL SOURCE:
        (A) ORGANISM: Homo sapiens
        (B) STRAIN: MKN45

(ix) FEATURE:
        (A) NAME/KEY: coding sequence (B) LOCATION: 1 to 759
(C) IDENTIFICATION METHOD: by experiment
(A) NAME/KEY: signal peptide
(B) LOCATION: 1 to 81
(C) IDENTIFICATION METHOD: by experiment
(A) NAME/KEY: mature peptide
(B) LOCATION: 82 to 759
(C) IDENTIFICATION METHOD: by experiment (x) SEQUENCE DESCRIPTION: SEQ ID NO: 4:

| ATG | GCG | CAG | CTG | TGC | GGG | CTG | AGG | CGG | AGC | CGG | GCG | TTT | CTC | GCC | CTG | 48 |
|---|---|---|---|---|---|---|---|---|---|---|---|---|---|---|---|---|
| Met | Ala | Gln | Leu | Cys | Gly | Leu | Arg | Arg | Ser | Arg | Ala | Phe | Leu | Ala | Leu | |
| 1 | | | | 5 | | | | | 10 | | | | | 15 | | |

| CTG | GGA | TCG | CTG | CTC | CTC | TCT | GGG | GTC | CTG | GCG | GCC | GAC | CGA | GAA | CGC | 96 |
|---|---|---|---|---|---|---|---|---|---|---|---|---|---|---|---|---|
| Leu | Gly | Ser | Leu | Leu | Leu | Ser | Gly | Val | Leu | Ala | Ala | Asp | Arg | Glu | Arg | |
| | | | 20 | | | | | 25 | | | | | 30 | | | |

| AGC | ATC | CAC | GAC | TTC | TGC | CTG | GTG | TCG | AAG | GTG | GTG | GGC | AGA | TGC | CGG | 144 |
|---|---|---|---|---|---|---|---|---|---|---|---|---|---|---|---|---|
| Ser | Ile | His | Asp | Phe | Cys | Leu | Val | Ser | Lys | Val | Val | Gly | Arg | Cys | Arg | |
| | | 35 | | | | | 40 | | | | | 45 | | | | |

| GCC | TCC | ATG | CCT | AGG | TGG | TGG | TAC | AAT | GTC | ACT | GAC | GGA | TCC | TGC | CAG | 192 |
|---|---|---|---|---|---|---|---|---|---|---|---|---|---|---|---|---|
| Ala | Ser | Met | Pro | Arg | Trp | Trp | Tyr | Asn | Val | Thr | Asp | Gly | Ser | Cys | Gln | |
| | 50 | | | | | 55 | | | | | 60 | | | | | |

| CTG | TTT | GTG | TAT | GGG | GGC | TGT | GAC | GGA | AAC | AGC | AAT | AAT | TAC | CTG | ACC | 240 |
|---|---|---|---|---|---|---|---|---|---|---|---|---|---|---|---|---|
| Leu | Phe | Val | Tyr | Gly | Gly | Cys | Asp | Gly | Asn | Ser | Asn | Asn | Tyr | Leu | Thr | |
| 65 | | | | | 70 | | | | | 75 | | | | | 80 | |

| AAG | GAG | GAG | TGC | CTC | AAG | AAA | TGT | GCC | ACT | GTC | ACA | GAG | AAT | GCC | ACG | 288 |
|---|---|---|---|---|---|---|---|---|---|---|---|---|---|---|---|---|
| Lys | Glu | Glu | Cys | Leu | Lys | Lys | Cys | Ala | Thr | Val | Thr | Glu | Asn | Ala | Thr | |
| | | | | 85 | | | | | 90 | | | | | 95 | | |

| GGT | GAC | CTG | GCC | ACC | AGC | AGG | AAT | GCA | GCG | GAT | TCC | TCT | GTC | CCA | AGT | 336 |
|---|---|---|---|---|---|---|---|---|---|---|---|---|---|---|---|---|
| Gly | Asp | Leu | Ala | Thr | Ser | Arg | Asn | Ala | Ala | Asp | Ser | Ser | Val | Pro | Ser | |
| | | | 100 | | | | | 105 | | | | | 110 | | | |

| GCT | CCC | AGA | AGG | CAG | GAT | TCT | GAA | GAC | CAC | TCC | AGC | GAT | ATG | TTC | AAC | 384 |
|---|---|---|---|---|---|---|---|---|---|---|---|---|---|---|---|---|
| Ala | Pro | Arg | Arg | Gln | Asp | Ser | Glu | Asp | His | Ser | Ser | Asp | Met | Phe | Asn | |
| | | 115 | | | | | 120 | | | | | 125 | | | | |

| TAT | GAA | GAA | TAC | TGC | ACC | GCC | AAC | GCA | GTC | ACT | GGG | CCT | TGC | CGT | GCA | 432 |
|---|---|---|---|---|---|---|---|---|---|---|---|---|---|---|---|---|
| Tyr | Glu | Glu | Tyr | Cys | Thr | Ala | Asn | Ala | Val | Thr | Gly | Pro | Cys | Arg | Ala | |
| | 130 | | | | | 135 | | | | | 140 | | | | | |

| TCC | TTC | CCA | CGC | TGG | TAC | TTT | GAC | GTG | GAG | AGG | AAC | TCC | TGC | AAT | AAC | 480 |
|---|---|---|---|---|---|---|---|---|---|---|---|---|---|---|---|---|
| Ser | Phe | Pro | Arg | Trp | Tyr | Phe | Asp | Val | Glu | Arg | Asn | Ser | Cys | Asn | Asn | |
| 145 | | | | | 150 | | | | | 155 | | | | | 160 | |

| TTC | ATC | TAT | GGA | GGC | TGC | CGG | GGC | AAT | AAG | AAC | AGC | TAC | CGC | TCT | GAG | 528 |
|---|---|---|---|---|---|---|---|---|---|---|---|---|---|---|---|---|
| Phe | Ile | Tyr | Gly | Gly | Cys | Arg | Gly | Asn | Lys | Asn | Ser | Tyr | Arg | Ser | Glu | |
| | | | | 165 | | | | | 170 | | | | | 175 | | |

| GAG | GCC | TGC | ATG | CTC | CGC | TGC | TTC | CGC | CAG | CAG | GAG | AAT | CCT | CCC | CTG | 576 |
|---|---|---|---|---|---|---|---|---|---|---|---|---|---|---|---|---|
| Glu | Ala | Cys | Met | Leu | Arg | Cys | Phe | Arg | Gln | Gln | Glu | Asn | Pro | Pro | Leu | |
| | | | 180 | | | | | 185 | | | | | 190 | | | |

| CCC | CTT | GGC | TCA | AAG | GTG | GTG | GTT | CTG | GCG | GGG | CTG | TTC | GTG | ATG | GTG | 624 |
|---|---|---|---|---|---|---|---|---|---|---|---|---|---|---|---|---|
| Pro | Leu | Gly | Ser | Lys | Val | Val | Val | Leu | Ala | Gly | Leu | Phe | Val | Met | Val | |
| | | 195 | | | | | 200 | | | | | 205 | | | | |

| TTG | ATC | CTC | TTC | CTG | GGA | GCC | TCC | ATG | GTC | TAC | CTG | ATC | CGG | GTG | GCA | 672 |
|---|---|---|---|---|---|---|---|---|---|---|---|---|---|---|---|---|
| Leu | Ile | Leu | Phe | Leu | Gly | Ala | Ser | Met | Val | Tyr | Leu | Ile | Arg | Val | Ala | |
| | 210 | | | | | 215 | | | | | 220 | | | | | |

| CGG | AGG | AAC | CAG | GAG | CGT | GCC | CTG | CGC | ACC | GTC | TGG | AGC | TCC | GGA | GAT | 720 |
|---|---|---|---|---|---|---|---|---|---|---|---|---|---|---|---|---|
| Arg | Arg | Asn | Gln | Glu | Arg | Ala | Leu | Arg | Thr | Val | Trp | Ser | Ser | Gly | Asp | |
| 225 | | | | | 230 | | | | | 235 | | | | | 240 | |

| GAC | AAG | GAG | CAG | CTG | GTG | AAG | AAC | ACA | TAT | GTC | CTG | TGA | | | | 759 |
|---|---|---|---|---|---|---|---|---|---|---|---|---|---|---|---|---|
| Asp | Lys | Glu | Gln | Leu | Val | Lys | Asn | Thr | Tyr | Val | Leu | * | | | | |
| | | | | 245 | | | | | 250 | | | | | | | |

(2) INFORMATION FOR SEQ ID NO:5:

(i) SEQUENCE CHARACTERISTICS:
        (A) LENGTH: 20 nucleotides (B) TYPE: nucleic acid
(C) STRANDEDNESS: single
(D) TOPOLOGY: linear (ii) MOLECULE TYPE: other nucleic acid, synthetic DNA (x) SEQUENCE DESCRIPTION: SEQ ID NO: 5:

AAGGTKGTKG GKMGKTGYMG  20

(2) INFORMATION FOR SEQ ID NO:6:

(i) SEQUENCE CHARACTERISTICS:
(A) LENGTH: 21 nucleotides
(B) TYPE: nucleic acid
(C) STRANDEDNESS: single
(D) TOPOLOGY: linear (ii) MOLECULE TYPE: other nucleic acid, synthetic DNA (x) SEQUENCE DESCRIPTION: SEQ ID NO: 6:

CKCCGTAKAC GAAKARYTGR C  21

(2) INFORMATION FOR SEQ ID NO:7:

(i) SEQUENCE CHARACTERISTICS:
(A) LENGTH: 252 amino acids
(B) TYPE: amino acid
(D) TOPOLOGY: linear (ii) MOLECULE TYPE: peptide (x) SEQUENCE DESCRIPTION: SEQ ID NO: 7:

```
Met Ala Gln Leu Cys Gly Leu Arg Arg Ser Arg Ala Phe Leu Ala Leu
 1               5                  10                  15

Leu Gly Ser Leu Leu Ser Gly Val Leu Ala Ala Asp Arg Glu Arg
             20                  25                  30

Ser Ile His Asp Phe Cys Leu Val Ser Lys Val Val Gly Arg Cys Arg
             35                  40                  45

Ala Ser Met Pro Arg Trp Trp Tyr Asn Val Thr Asp Gly Ser Cys Gln
         50                  55                  60

Leu Phe Val Tyr Gly Gly Cys Asp Gly Asn Ser Asn Asn Tyr Leu Thr
 65                  70                  75                  80

Lys Glu Glu Cys Leu Lys Lys Cys Ala Thr Val Thr Glu Asn Ala Thr
                 85                  90                  95

Gly Asp Leu Ala Thr Ser Arg Asn Ala Ala Asp Ser Ser Val Pro Ser
                100                 105                 110

Ala Pro Arg Arg Gln Asp Ser Glu Asp His Ser Ser Asp Met Phe Asn
                115                 120                 125

Tyr Glu Glu Tyr Cys Thr Ala Asn Ala Val Thr Gly Pro Cys Arg Ala
        130                 135                 140

Ser Phe Pro Arg Trp Tyr Phe Asp Val Glu Arg Asn Ser Cys Asn Asn
145                 150                 155                 160

Phe Ile Tyr Gly Gly Cys Arg Gly Asn Lys Asn Ser Tyr Arg Ser Glu
                165                 170                 175

Glu Ala Cys Met Leu Arg Cys Phe Arg Gln Gln Glu Asn Pro Pro Leu
                180                 185                 190

Pro Leu Gly Ser Lys Val Val Leu Ala Gly Leu Phe Val Met Val
                195                 200                 205

Leu Ile Leu Phe Leu Gly Ala Ser Met Val Tyr Leu Ile Arg Val Ala
        210                 215                 220

Arg Arg Asn Gln Glu Arg Ala Leu Arg Thr Val Trp Ser Ser Gly Asp
```

-continued

|  | 225 |  |  |  | 230 |  |  |  | 235 |  |  | 240 |
|---|---|---|---|---|---|---|---|---|---|---|---|---|
| Asp | Lys | Glu | Gln | Leu | Val | Lys | Asn | Thr | Tyr | Val | Leu | |
|  |  |  |  | 245 |  |  |  |  | 250 |  |  | |